United States Patent [19]

Porter et al.

[11] Patent Number: 5,785,978
[45] Date of Patent: Jul. 28, 1998

[54] SKIN CARE COMPOSITIONS AND METHODS

[75] Inventors: Steven S. Porter; Francine E. Porter. both of Denver, Colo.

[73] Assignee: Osmotics Corporation. Denver, Colo.

[21] Appl. No.: 687,122

[22] Filed: Jul. 24, 1996

Related U.S. Application Data

[63] Continuation-in-part of Ser. No. 339,553, Nov. 15, 1994, abandoned, and Ser. No. 414,345, Mar. 31, 1995, abandoned.

[51] Int. Cl.$^6$ .............. A61K 6/00; A61K 13/00
[52] U.S. Cl. .............. 424/401; 424/448; 424/449; 514/845
[58] Field of Search ............. 424/401, 448, 424/449; 514/845

[56] References Cited

U.S. PATENT DOCUMENTS

| | | | |
|---|---|---|---|
| 4,073,291 | 2/1978 | Maruel | 128/155 |
| 4,585,797 | 4/1986 | Cioca | 514/773 |
| 4,655,767 | 4/1987 | Woodard et al. | 604/896 |
| 4,748,976 | 6/1988 | Cali | 128/156 |
| 4,840,796 | 6/1989 | Sweet et al. | 424/448 |
| 4,895,727 | 1/1990 | Allen | 424/642 |
| 4,951,657 | 8/1990 | Pfister et al. | 128/156 |
| 4,983,382 | 1/1991 | Wilmott et al. | 424/62 |
| 4,999,348 | 3/1991 | Cioca et al. | 514/171 |
| 5,026,552 | 6/1991 | Gueret | 424/401 |
| 5,064,655 | 11/1991 | Uster et al. | 424/450 |
| 5,091,171 | 2/1992 | Yu et al. | 424/642 |
| 5,144,944 | 9/1992 | Rice | 602/74 |
| 5,232,702 | 8/1993 | Pfister et al. | 424/448 |
| 5,238,965 | 8/1993 | Piazza et al. | 514/844 |
| 5,296,500 | 3/1994 | Hillebrand | 514/562 |
| 5,330,757 | 7/1994 | Burke | 424/449 |
| 5,360,824 | 11/1994 | Barker | 424/680 |
| 5,595,984 | 1/1997 | Blank | 514/159 |

FOREIGN PATENT DOCUMENTS

94/00098  1/1994  WIPO.
94/00109  1/1994  WIPO.

OTHER PUBLICATIONS

Tanaka et al. (1992) "The Effect of Reactive Oxygen Species on the Biosynthesis of Collagen and Glycosaminoglycans in Cultured Human Dermal Fibroblasts." *Arch. Dermatol. Res.* 285: 352–355.

Pfister et al. (Sep. 1990) "Permeation Enhancers Compatible with Transdermal Drug Delivery Systems: Part I: Selection and Formulation Considerations." *Pharmaceutical Technology*.

Pfister et al. (Oct. 1990) Permeation Enhancers Compatible with Transdermal Drug Delivery Systems: Part II: System Design Considerations.

Pfister et al. (Jan. 1992) "Developing Drug–Compatible Adhesives for Transdermal Drug Delivery Devices." *Pharmaceutical Technology*, pp. 42–58.

(1994) "Wrinkies & Frownies." *Vermont Country Store Catalog*, p. 65.

Pfister et al. (Mar. 1989) "Customizing Silicone Adhesives for Transdermal Drug Delivery Systems." *Pharmaceutical Technology*.

(List continued on next page.)

*Primary Examiner*—D. Gabrielle Phelan
*Attorney, Agent, or Firm*—Davis Graham & Stubb LLP

[57] ABSTRACT

Skin care compositions and methods are provided for improving the appearance of skin affected by aging, photodamage and/or oxidative stress. Specifically, adhesive materials containing cosmetically active ingredients, e.g., one or more antioxidants such as Vitamins A, C and/or E, or moisturizers are applied in concentrated dry powdered form to target areas including the frownline area of the forehead, the front of the neck, the crows-feet area near the eyes, the upper lip and the nasolabial area using a transdermal patch having an acidity approximating human skin acidity of 5.5, preferably by an appropriate ratio of ascorbic acid and ascorbate salts.

21 Claims, 9 Drawing Sheets

OTHER PUBLICATIONS

Ames et al. (1993) "Oxidants, Antioxidants, and the Degenerative Diseases of Aging," *Proc. Natl. Acad. Sci*, USA, vol. 90 pp. 7915–7922.

Bast et al (1991) "Oxidants and Antioxidants: State of the Art," *The American Journal of Medicine*, vol. 91, pp. 3C–2S–3C–12S.

Kretz A. (1992), "Vitamin A in Cosmetics."

Idson (May 1990) "Vitamins in Cosmetics, An Update, I. Overview and Vitamin A," *DCI*, pp. 26, 28, 91.

Baker et al. "Materials Selection for Transdermal Delivery Systems," in *Transdermal Drug Delivery*, eds. Hadgraft and Guy, Marcel Dekker, New York, pp. 293–311 (1991).

Anderson et al. (1991) "The Effects of Ascorbic Acid on Collagen Synthesis by Cultured Human Skin Fibroblasts," *Biochem. Soc. Trans.*, pp. 485.

Idson (Aug. 1990), "Vitamins in Cosmetic an Update Part II: Vitamin E," *DCI*, p. 20 et al.

Idson (Jul. 1985), "Percutaneous Absorption Enhancers," *D&CI*, p. 30 et al.

Darr et al. (1993), "Ascorbic Acid and Collagen Synthesis: Rethinking a Role for Lipid Peroxidation," *Archives of Biochemistry and Biophysics*, vol. 307, No. 2, pp. 331–335.

Geesin et al. (1990), "Retinoids Affect Collagen Synthesis Through Inhibition of Ascorbate–Induced Lipid Peroxidation in Cultured Human Dermal Fibroblasts," *Archives of Biochemistry and Biophysics*, vol. 278, No. 2, pp. 350–355.

Kristal et al. (1992), "An Emerging Hypothesis: Synergistic Induction of Aging by Free Radicals and Maillard Reactions," *Journal of Gerontology, Biological Sciences*, vol. 47, B107–B114.

Katz, M. (1986), "The Expanding Role of Oxygen Free Radicals in Clinical Medicine," *The Western Journal of Medicine*, pp. 441–445.

Wilson, R. (Jan. 1992), "Why the Concern About Free Radicals?" *DCI*.

Wilson, R., "Marine Extracts in Cosmetics", *DCI*, pp. 30, 32, (1990).

Fox, Marisa, "Pushing Patches," *Harper's Bazaar*, 80, 82, Apr., 1995.

SKIN CARE COMPOSITIONS AND METHODS

REFERENCE TO RELATED APPLICATIONS

This application is a Continuation-in-Part of U.S. patent application Ser. No. 08/339,553 filed Nov. 15, 1994 now abandoned, and Ser. No. 08/414,345 filed Mar. 31, 1995 now abandoned.

FIELD OF THE INVENTION

This invention relates to skin care compositions and methods for the improvement of the appearance of aging skin and, in particular, to the improvement of wrinkling skin in target areas including but not limited to the areas outside and under the eyes, in the nasolabial area, the upper lip, the forehead, the neck and the hands.

BACKGROUND OF THE INVENTION

The population in general is very concerned with maintaining youthful and attractive appearances. As the average age of the population of this country increases, it is anticipated there will be an increasing market for skin care products which can improve the appearance of aging skin and/or maintain attractive skin qualities. Treatments designed to prolong or promote youthful appearance include topical applications of cosmetic preparations, lotions and moisturizer, electrical stimulation, collagen injections and cosmetic surgery.

With aging, prolonged or repeated exposure to ultraviolet radiation, and/or oxidative stress, the skin of the face often shows signs of damage. Aging or other damage to skin may be recognized by effects including wrinkling, yellowing, taxing, lines, spots, mottling and a leathery or dry appearance. At the histological level, skin damage, e.g., from photoaging, may be reflected in tangled, thickened, abnormal elastic fibers, decreased collagen and increased glycosaminoglycan content (Tanaka et al. (1993) *Arch. Dermatol. Res.* 285:352–355). The aging process results in thinning and deterioration of the skin. There is a reduction in cells and in blood supply, and a flattening in the junction between the dermis and epidermis.

Ascorbic acid (Vitamin C), Vitamin A, tocopherol (Vitamin E) and β-carotene, which can at least in part be functionally characterized as antioxidants, are essential to the maintenance of a healthy and attractive skin appearance in humans. Vitamin K is also beneficial to maintaining attractive skin. Generally, these nutrients are obtained in the diet and/or in nutritional supplements. Other cosmetically beneficial components can be applied topically for improving skin appearance and quality; such components include moisturizers, including but not limited to polysaccharides and marine extracts.

The aforementioned antioxidants help to prevent damage to skin and/or body organs resulting from poor nutrition, physiological processes and exposure to environmental pollutants, certain drugs, alcohol, and ultraviolet (UV) radiation. Normal physiological processes, including aging, and exposure to deleterious agents can lead to the generation of free oxygen radicals, a component of so-called oxidative stress. Oxidative stress leads to damage to cellular membranes, the genetic material and other cellular targets including connective tissue and collagen. Other sources of oxidative stress include heat, trauma, infection, hyperoxia, toxins and excessive exercise. Antioxidants can donate electrons without generating potentially harmful chain reactions and oxidation of cellular components, and thus provide protection from oxidative damage. A further problem, especially with aging skin, is a decrease in blood circulation.

Ascorbic acid (Vitamin C) is known to stimulate and/or regulate collagen synthesis in human tissue. When collagen synthesis is stimulated in skin, a healthier and younger skin appearance results. Ascorbic acid can also help to prevent or minimize UV-induced lipid oxidation, thus providing further benefits in maintaining or promoting attractive skin appearance. Further, ascorbic acid acts to inhibit melanin synthesis, which leads to skin discoloration during the aging process, and to inhibit histamine release from cellular membranes, which is associated with allergenic reactions, particularly among individuals with so-called "sensitive skin."

Ascorbic acid-containing compositions for topical application to the skin have been described (see, e.g., U.S. Pat. No. 4,983,382, issued Jan. 8, 1991; Avon Products, Inc.). U.S. Pat. No. 4,999,348, issued Mar. 12, 1994, Estee Lauder, Inc., refers to cholesteric liquid crystal compositions for controlled release and enhanced penetration of biologically active materials such as Vitamin A to the skin. Vitamin A is said to make wrinkling in the skin less noticeable. U.S. Pat. No. 5,238,965, issued Aug. 24, 1993, Procter & Gamble Company, refers to regulating wrinkling using topical applications of lipophosphatidic acid compositions. WO 94/00109 and WO 94/00098 (Lancaster Group AG), both incorporated by reference, refer to dermatological agents for increasing oxygen transport in the skin; these agents comprise phospholipids and oxygen-loaded fluorocarbons. U.S. Pat. No. 5,296,500 (issued Mar. 22, 1994, Proctor & Gamble Co.) claims methods for regulating wrinkles or atrophy of the skin using compositions comprising N-acetyl cysteine, including compositions where one or more additional components (sunscreen, antioxidants, anti-inflammatory agents) are added. United Kingdom Patent Application GB 2 265 086 A describes a whitening agent applied to the skin utilizing a transdermal patch. The present invention has the advantage over these conventional preparations in that absorption of Vitamin C or other wrinkle treatment into the skin can continue over an extended period of time without the extra effort or inconvenience of needing to actively apply another coat of a lotion, cream or the like.

Tocopherol (Vitamin E, with α-tocopherol being the most potent) has effects in the skin including antioxidant activity, improved membrane stability, protection against UV radiation and nitrosamine formation, moisturizing action on dry skin and anti-inflammatory action. It is the antioxidant effect which is believed most important in protection from oxidative damage. Tocopherol has also been shown to play a role in maintaining the structural integrity of cell membranes and connective tissue. Firmness, texture and/or tone are maintained by the integrity of the elastic fiber in the dermis and collagen in connective tissue. Vitamin E is also believed to improve the hydration of the skin, and insufficiently hydrated skin is characterized by lines at relatively closer distance than in normal skin, irregular texture and a "scruffy" appearance.

It has been reported that only about 20–40% of oral vitamin E is absorbed, and it is not known what fraction of the absorbed vitamin E is available to the skin. Topically applied vitamin E, either in the alcohol or the acetate form, can be absorbed through the skin. When combined with ascorbyl palmitate which acts as an oxygen scavenger, tocopherol is particularly effective as an antioxidant to extend the shelf-life of natural products formulations such as perfumes, vitamins and herbal extracts.

β-carotene within physiologically advantageous levels is also essential for skin development. An excess of β-carotene inhibits the keratinization of epithelial tissue, and a deficiency results in acne-like blackheads. β-carotene also acts to improve the skin's water barrier properties, and therefore β-carotene can be useful in treating seasonal and/or environmental problems (heat, dryness, air pollution). Provision of β-carotene to the skin will increase the amount of Vitamin A within the skin, and thereby impart beneficial effects on appearance of skin.

Other cosmetically active compositions, when topically applied to the skin, include marine extracts and moisturizers, for example, hyaluronic acid. Marine extracts, for example, those prepared from seaweed, are rich in minerals, amino acids, vitamins, and polysaccharides which are believed to function as moisturizing agents. Additional embodiments of a skin care patch can increase the oxygen supply to the skin, for example, using oxygen-loaded fluorocarbon compounds (as disclosed in WO 94/00109, WO 94/00098, for example) within the patch. Further embodiments include patches comprising cosmetically effective amounts of an active ingredient such as lysophosphatidic acid, an α-hydroxyacid and N-acetyl cysteine.

Transdermal delivery of pharmaceutical compositions is well known. Such well-known pharmaceutical compositions include scopolamine for treatment of motion sickness, estrogen replacement therapy and nicotine for assistance in breaking tobacco habits. The present invention is believed to be the first application of transdermal delivery systems for skin care and the improvement of the appearance of aging, photodamaged or oxidatively stressed skin, especially for the improvement of the appearance of wrinkled skin.

SUMMARY OF THE INVENTION

It is an object of this invention to provide cosmetic compositions and methods for improving the appearance of aging skin or skin damaged, such as by overexposure to oxidative stress, sunlight or ultraviolet light. With treatment, the appearance of the wrinkling of the skin becomes less apparent. Other outward indications of aging, photodamage or oxidative stress to the skin such as mottling, laxness, spots, dryness or leatheriness can also be lessened or slowed. The method of this invention is the percutaneous (or intradermal) delivery to the skin of cosmetically active compositions including antioxidants, for example, ascorbic acid, vitamin A, vitamin E, β-carotene or a combination thereof, via a transdermal delivery device. Other cosmetically active ingredients which can be incorporated into a transdermal (or intradermal) delivery device for sustained application to the skin include moisturizers (e.g. hyaluronic acid) and marine extracts from kelp and/or algae, essential fatty acids, collagen and lipids.

Preferably, the antioxidant is Vitamin C, from 20 to 200 mg per square inch in an adhesive matrix. More preferably ascorbic acid is formulated with a cosmetically acceptable salt of ascorbic acid in proportions such that the pH of the combination in solution is about 4 to about 7, preferably, about 5 to about 6, most preferably about 5.5. Those salts include, but are not limited to, sodium ascorbate, potassium ascorbate and calcium ascorbate, preferably sodium ascorbate. Where sodium ascorbate is combined with ascorbic acid in the matrix, the preferred ratio is from about 1:20 to about 1:25 of acid sodium ascorbate, and, preferably about 1:22.

Preferably, the delivery device is adhered to the skin using a pressure sensitive adhesive, but other adhesives are known to the art, including but not limited to, natural, isobutyl and butyl rubber compositions and acrylate-based adhesives and pressure sensitive adhesives. The configuration of the delivery device for the sustained delivery of cosmetically active ingredients to the skin can be adhesive matrix, liquid or solid state reservoir or polymer matrix; the preferred delivery device is the adhesive matrix type. In an adhesive matrix type patch, there is an impermeable backing, a matrix comprising the cosmetically active ingredient, optionally comprising a permeation enhancer and/or an anti-irritant, and a release liner.

In most transdermal delivery systems, thin, flexible occlusive films serve as protective backing substrate and release liner. For the present skin care applications, an occlusive protective backing substrate is preferred over a non-occlusive backing substrate. The materials used for liner and backing provide storage stability by keeping the active ingredients from migrating into or through the backing material and liner before use. The patches of the present invention desirably have the following tape properties: release or peel force<50 g/cm; tack value>50 g/cm; adhesion force 100–1200 g/cm; release force<1 g/cm; preferably the adhesion force is about 50–300 g/cm and the shear force is about 14 kg/6.25 cm². Preferably, the adhesive is medical grade. The peel force required to remove the release liner from the patch should be sufficient to prevent inadvertent separation of the liner from the patch before use and low enough so that it can be readily removed by the intended user.

Where an acrylic adhesive is used, that adhesive is medical grade and rated between 0 and 2, preferably between 0 and 1 on the Draize Code Scale. On this scale a score of 0 means no erythema (reddening) and no edema (swelling when a test patch is applied to the skin and removed. The acrylic adhesive can optionally include a cross-linking agent.

Liquid and solid state reservoir transdermal delivery devices are configured so that the reservoir comprising the cosmetically active ingredients, enhancers and any other formulation ingredients is located between the backing material and the adhesive, and during use, formulation ingredients pass through the adhesive and then into the skin. Compatibility of various excipients and penetration enhancers with adhesives are well known to the art, and the skilled artisan can readily choose suitable concentrations and combinations of ingredients and adhesives.

A typical non-silicone polymer matrix transdermal delivery device has a rim of adhesive so that the penetration enhancer, cosmetically active ingredient(s) and other formulation ingredients are not fully in contact with the adhesive. In the preferred embodiment, the entire patch is adhesive and contains at least one cosmetically active ingredient. One surface is applied to the intended position on the face with gentle pressure to promote adhesion, after removal of a release liner. The other surface (away from the skin) is covered with a protective backing during storage before use and during use.

Where desired, the skin care patches of the present invention optionally comprise formulation ingredients which either increase or decrease the release rates and/or absorption rates of the cosmetically active ingredients. Water soluble additives which increase release rate include ethylene glycol, glycerine, polyethylene glycols 200, 400, 600; polysorbate 80, lactose, gelatin, sucrose, sodium alginate, carboxymethyl cellulose, ammonium chloride, and polyvinylpyrrolidone. Lipid soluble additives which tend to increase release rate include cholesterol. Certain surfactants also have the effect of increasing release rate; these surfactants include sodium lauryl sulfate, dodecyltrimethylammonium chloride and azone. Release rates can be decreased by the addition of compounds including such fillers as kaolin, Sephadex G-25 (high pressure liquid chromatography gel filtration resin) and silica.

The most preferred embodiment of the present invention utilizes ascorbic acid and sodium ascorbate in a dry powder form suspended in a dry matrix. The ascorbic acid and sodium ascorbate in such a form is highly concentrated the 85–88% range, more so than in common liquid compositions in which the ascorbic acid is diluted by the liquid suspension. The highly concentrated ascorbic acid is buffered to a pH of about 5.5 with the dry powder sodium ascorbate. The system thus is capable of applying highly concentrated ascorbic acid and, but within a skin-compatible pH. The natural moisture of the skin causes the powdered ingredients to go into solution from the dry matrix and be absorbed into the skin surface. The occlusive protective backing ensures that the active ingredient is isolated from the atmosphere during the treatment procedure. Similar systems could employ other antioxidants such as potassium ascorbate, calcium ascorbate; magnesium ascorbate and ascorbate palmitate.

Figure 1:
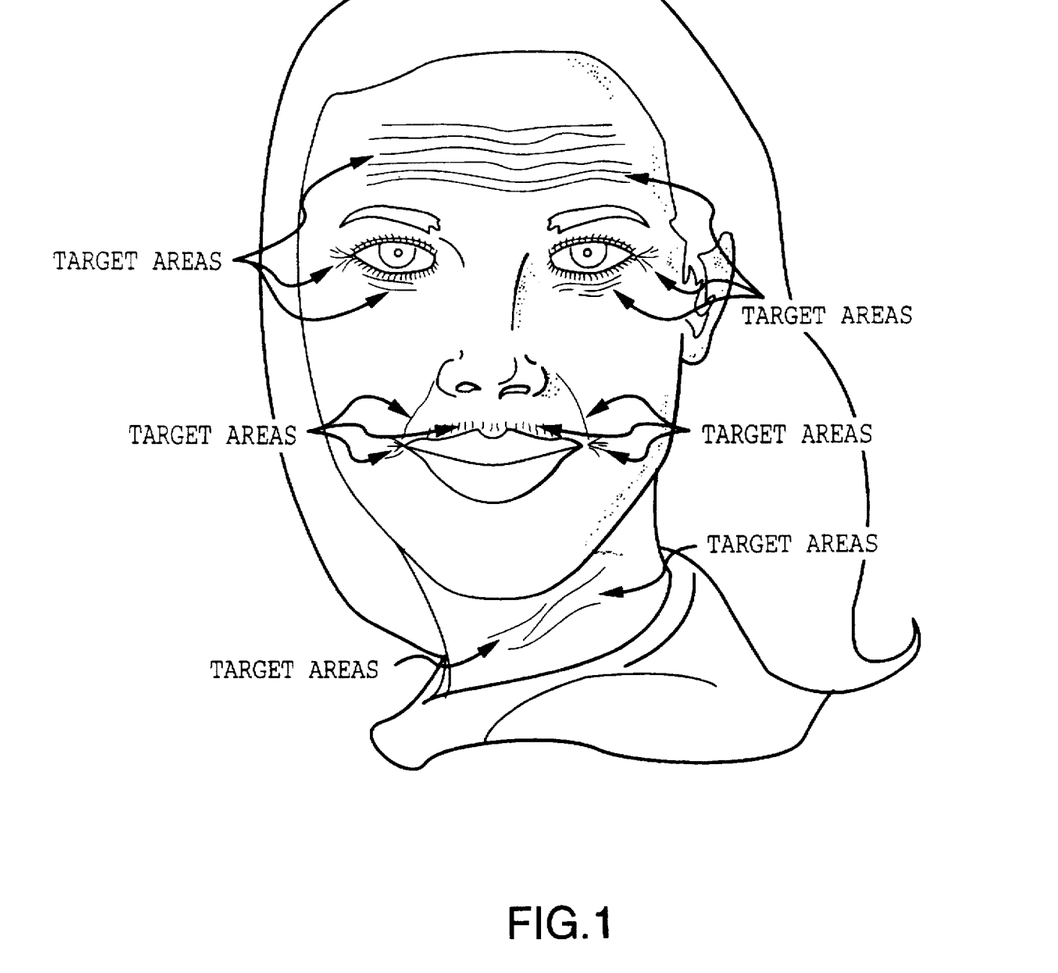
FIG. 1 is a sketch of a typical aging human face with wrinkles under and in the outside corners of the eyes, the forehead, upper lip, the area from the outside bottom edges of the nose to the outside corners of the mouth (the nasolabial fold area) and the neck.
Figure 2:
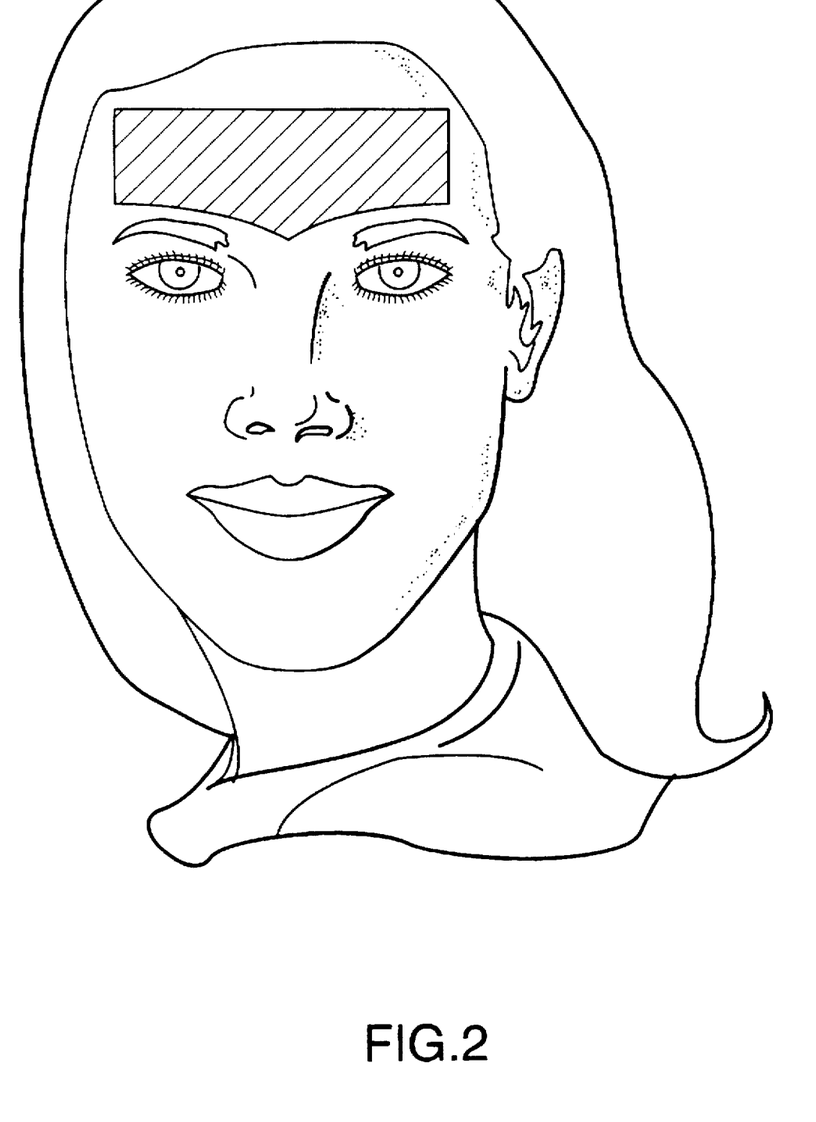
FIG. 2 illustrates a human face with the transdermal delivery device for application of cosmetically active compositions in place on the forehead.

Preferably, the skin care transdermal or intradermal delivery devices (patches) are shaped specifically for the target skin area to be treated. A generally rectangular with chevron patch is advantageously applied to the lower forehead area, an example of which is illustrated in FIG. 2. For application beneath and at the outer corners of the eye a generally kidney-shaped patch is used, and the shapes for the right and left sides are mirror images of one another. For the nasolabial fold area, the patch is shaped substantially like a boomerang, generally kidney-shaped. Skin care patches are also provided which fit the back of the hand, optionally with extensions down the fingers. FIGS. 2–7 illustrate human faces and hands with the aforementioned anatomically designed skin care patches in place.

DETAILED DESCRIPTION OF THE INVENTION

A transdermal or intradermal delivery device, known colloquially as a patch, is a unit which adheres to the skin of an individual, and allows for sustained release of an active ingredient into the skin, from which the active ingredient usually enters systemic circulation. Types of patches include liquid reservoir, solid state reservoir, polymer matrix, adhesive matrix and wet wick patches, depending on the configuration of the active ingredients and the patch materials. The active ingredients in an intradermal delivery device for improving the appearance of aging or photodamaged skin can include one or more of the following: alpha hydroxyacids, alpha ketoacids and polymeric hydroxyacids, moisturizers, collagen, marine extract and antioxidants including one or more of a tocopherol (Vitamin E), β-carotene, Vitamin A and Vitamin C (and/or cosmetically acceptable salts thereof), and are generically termed cosmetically active ingredients herein. A preferred tocopherol compound is α-tocopherol. Additionally or alternatively, cosmetic benefits may be obtained by the use of skin care patches comprising molecules (e.g., fluorocarbons) capable of improving oxygen supply in skin tissue, as described, e.g., in WO 94/00098 and WO 94/00109.

Because of the beneficial effects of various cosmetically active ingredients, it has been a longstanding objective of skin care products to deliver effective concentrations of the active ingredients to the skin's tissue matrix (the dermal layers) via the most effective method possible to achieve maximum skin appearance benefits. Topical application of cosmetically active ingredients including but not limited to antioxidants, moisturizers and marine extracts via a transdermal delivery device has several advantages over topical application of a conventional formulation such as a lotion, creme or ointment in that with a patch, application is passive and continuous delivery of the active ingredient can be achieved for up to 24 hrs, or longer. Conventional topical application is limited by the amount of lotion, etc. which is administered, the amount of the active ingredient which penetrates and the depth to which it penetrates, oxidation of the active ingredients before or during penetration and evaporative loss of solvents and/or active ingredients from lotions and the like. With a patch, evaporation is minimal, even when a non-occlusive patch is used.

Skin care patches can also include cosmetically active ingredients other than antioxidants; for example, one or more of marine extracts, moisturizers and collagen, with or without a penetration enhancer, can be loaded in the reservoir, matrix or wet wick transdermal patch. Moisturizers can be one or more of hyaluronic acid, marine extract (of kelp and/or algae), fatty acids, lipids, and glycerides. Alpha hydroxyacids, alpha keto acids and polymeric hydroxyacids, for example, as described in U.S. Pat. No. 5,091,171 (Yu and Van Scott), which is incorporated by 30 reference herein, can be incorporated into the adhesive matrices of skin care patches to ameliorate the unattractive effects of aging, photodamage or oxidative stress.

The active antioxidant ingredients for cosmetic patch compositions are present in a cosmetically effective amount, preferably from about 30–1000 mg per patch. Ascorbic acid (and/or a cosmetically acceptable salt thereof), tocopherol, Vitamin A and β-carotene are preferred antioxidants. Taurine can also be used. Preferably, each active ingredient is present at about 30–60 mg per square inch.

A preferred matrix-type skin care patch contains a cosmetically effective amount of an antioxidant (Vitamin C or E or β-carotene), preferably Vitamin C (and/or a cosmetically acceptable salt), and preferably at a concentration of about 2–50% (about 60 mg per square inch), optionally with a penetration enhancer present at a concentration of about 1–10% by weight.

The patch itself is preferably made of polymeric material. Preferably the patch is made of a polymeric material which is chemically and biologically inert, non-toxic, non-irritating, non-sensitizing, non-allergenic and has adhesive properties which are easily manipulated. The patch material should further be flexible, with good cohesive strength (shear strength of >5 kg/6.25 cm), suitable and easily controlled tack properties, low release force so that it can be readily removed from the liner backing and easily manipulated skin adhesion. The patch should have tack and adhesive properties which allow rapid adherence to the skin after minimal application of gentle hand pressure, and the matrix should rapidly mold itself closely with the contours of the target skin for best transfer of active ingredients. Adhesion properties can be determined using techniques well known to the art, for example using a digital probe tack tester (e.g., Polyken, Testing Machines, Amityville, N.Y.) and as described in Pfister et al., Pharmaceutical Technology, January 1992, pp. 42, 46. The desired adhesion of the pressure sensitive adhesive is between about 50 and 300 g/cm, preferably 80–300 g/cm. If the adhesion is above this level, then the adhesive is too aggressive to the skin. If the adhesion is below this level, then the patch may fall off. An impermeable film is bound to the surface of the patch destined to be away from the skin during use; a release liner is bound to the surface of the patch destined to be applied to the skin during use, and the release liner is removed prior to use. The impermeable film is not permeable to the active ingredient(s), but it may be occlusive, or more preferably, nonocclusive. The skilled artisan understands how to manipulate the adhesive composition in combination with the active ingredients so as to maintain desirable adhesive properties and effective delivery of the cosmetically active ingredient(s).

Adhesives, e.g., acrylic adhesives and pressure sensitive adhesives can be rated according to the Draize Dermal Scoring Code. A score of 0 means there is no erythema or edema after test application; 1 means barely perceptible reddening or swelling; 2 means well defined erythema or slight edema; 3 means moderate to severe erythema or moderate edema (raised 1 mm); and 4 reflects severe erythema (beet redness) to slight eschar formation and severe edema (raised >1 mm and extending beyond the area of exposure). Nontoxic adhesives with Draize Code Scores of 0–1 are deemed suitable for use on premature infants, and such medical adhesives can also be used in the skin care patches of the present invention without injuring or irritating the relatively delicate facial and neck target skin areas. Medical acrylate adhesives and/or medical acrylic pressure sensitive adhesives with Draize scores of 0–1 are well known and commercially available.

The acrylate-based matrix preferably contains medical acrylate adhesive, preferably pressure-sensitive adhesive, and active ingredient in a ratio of from about 40:60 to about 60:40, preferably about 50:50 by weight. It is understood that the incorporation of the cosmetically active ingredient into the adhesive may change the adhesion of the matrix composition relative to adhesive alone. Adjusting (increasing) the thickness of the matrix composition can compensate for some loss of adhesiveness.

The surface of the transdermal or intradermal delivery device which is away from the skin may be non-occlusive, i.e., permeable to air and/or water, or it may be occlusive, i.e., non-permeable to water vapor.

Reference may be made to U.S. Pat. Nos. 4,840,796 (Sweet et al.), 4,951,657 (Pfister et al.), 4,655,767 (Woodard et al.) and/or 5,232,702 (Pfister et al.), all incorporated by reference herein, for discussion of transdermal delivery devices and pressure-sensitive adhesive compositions for use in such devices.

The ascorbic acid-containing skin care delivery device is specifically exemplified in Example 2. Other antioxidant compounds (e.g., tocopherol or Vitamin A) can be substituted in the formulation for the ascorbic acid.

The nature of the adhesive on the side of the patch applied to the skin is important. It is preferably chemically and biologically inert, not toxic, irritating or sensitizing, moisture resistant, and it should have minimal cold flow for easy removal, it should be flexible, suitable tack for quick sticking but easily removed and restuck when adjustments are necessary during application, and have low release force for easy removal of the liner. The adhesive should be non-irritating to the skin, and the adhesiveness should be sufficient to adhere the patch to the skin for at least from about 7 to about 12 hrs, but the patch should not adhere to the skin so tightly that the force required to remove it results in skin damage due to pulling or stretching of the skin. The skilled artisan knows how to choose cohesive strength, creep resistance, end-use tape properties, including tack, peel force and skin adhesion, commensurate with the application to and removal from delicate facial skin.

Preferred rheological properties for the adhesive-active ingredient matrix described in Example 2.3, at a frequency of 0.01 and a temperature of 30° C., are as follows:

G' (storage, or elastic, modulus) about $1\times10^8$ to about $1\times10^9$, preferably about $6\times10^8$;

G" (loss or fluid modulus) about $3\times10^6$–$1.4\times10^7$, preferably about $7$–$9\times10^6$; and N° (intrinsic viscosity) of about $4\times10^8$–$4\times10^9$, preferably about $7\times10^8$–$2\times10^9$.

Although ascorbic acid matrix-type patches are effective for ameliorating the appearance of wrinkled skin, for example, wrinkled facial skin, there may be some irritation to the treated skin if the matrix does not contain a material which provides some buffering action or some partial neutralization of the acidity of the ascorbic acid when it dissolves into the skin. It is preferred that the pH of the ascorbic acid matrix composition is between about 4 and about 7, more preferably from pH about 4 to about 6, and most preferably, about pH 5.5, which is the pH of most human skin. This pH can be achieved by combining the ascorbic acid with an irritant buffer such as sodium bicarbonate, but the disadvantage is that buffer is not an active ingredient. It is desirable to use a non-irritating, non-toxic, freely soluble salt of ascorbic acid, including but not limited to, sodium ascorbate, potassium ascorbate, calcium ascorbate or magnesium ascorbate. Where sodium ascorbate is used in combination with ascorbic acid, the ratio (by weight) of ascorbic acid to sodium ascorbate should be from about 1:20 to about 1:25, preferably about 1:22. It is understood that when cations other than sodium are used, the ratio must be adjusted according to the dissociation constants in solution and other properties of the ascorbate salt. Potassium ascorbate and calcium ascorbate are useful in combination with ascorbic acid in the present formulations, with appropriate modifications in ratio to achieve the desired solution pH.

Preferably, a solution of ascorbic acid can be adjusted in pH to the desired range using an ascorbate salt, incorporated into the adhesive, and then dried so that the ascorbate and cations can be prepared as a dry powder for use in the present cosmetically active transdermal delivery devices.

Figure 8:
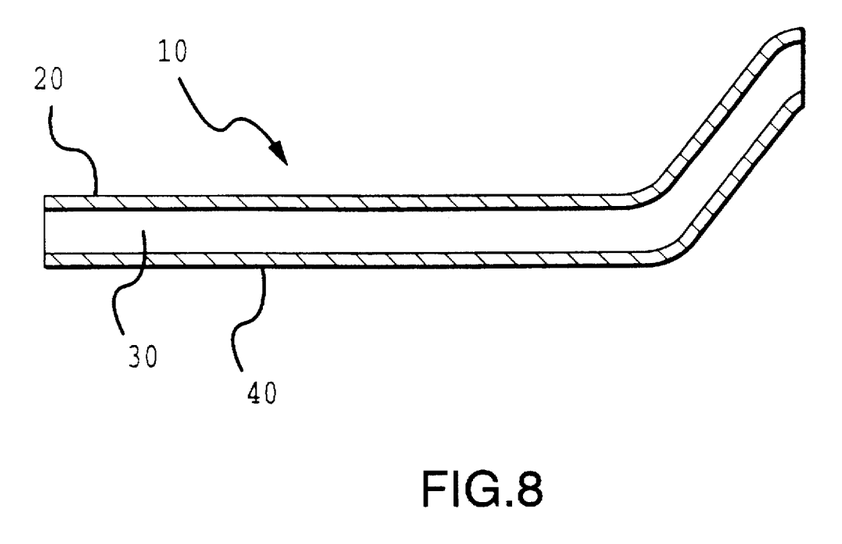
FIG. 8 shows a cross sectional view of a transdermal patch in accordance with the present invention.

A cross sectional view of a transdermal patch in accordance with the present invention is shown in FIG. 8. The patch 10 includes a release liner 20, adhesive layer 30 incorporating the biologically active material, and backing 40. The release liner 20 and the backing 40 are preferably occlusive, that is, impermeable to oxygen in the air. Such impermeability ensures that the biologically active material in the adhesive layer 30 remains biologically active before and during the treatment process by isolating it from the oxidizing effect of air in the atmosphere. The adhesive layer 30 is manufactured in a preferred embodiment in accordance with the procedures described above; ascorbic acid and an active buffering agent such as an ascorbate salt is mixed to a desired acidity of about 5.5 pH, applied to the adhesive material, and dried to a concentrated powder form using a drying oven or otherwise.

It is understood that for the present application the ascorbate salt will be non-toxic and not irritating and that it will be freely soluble in an aqueous environment. For the present purpose, these ascorbate compositions are termed cosmetically acceptable ascorbate salts. These include potassium, sodium, magnesium, and calcium salts.

It is also understood that other dermatologically acceptable compounds can be used to raise the solution pH of the matrix composition comprising ascorbic acid. Such compounds are non-toxic and non-irritating to the skin, and include, but are not limited to, sodium acid phosphate, sodium borate, sodium citrate and sodium acid tartrate. It is noted that these compounds do not individually provide any cosmetic benefit.

For the present cosmetic application, the patches are specifically sized and shaped according to the target area. Preferably, the ends or edges of the patches are to be rounded, rather than sharp angles or corners. For the forehead, where use of the patches of the present invention are used to ameliorate or prevent the appearance of "frown lines" on the lower forehead, the patch is to be in the shape of a shallow chevron (see FIG. 2). The width of the patch is from about 5 to about 6 inches, and the height of the patch is from about 1.0 inch to about 1.75 inches, with the angle of the curved chevron being from about 90° degrees.

Figure 3:
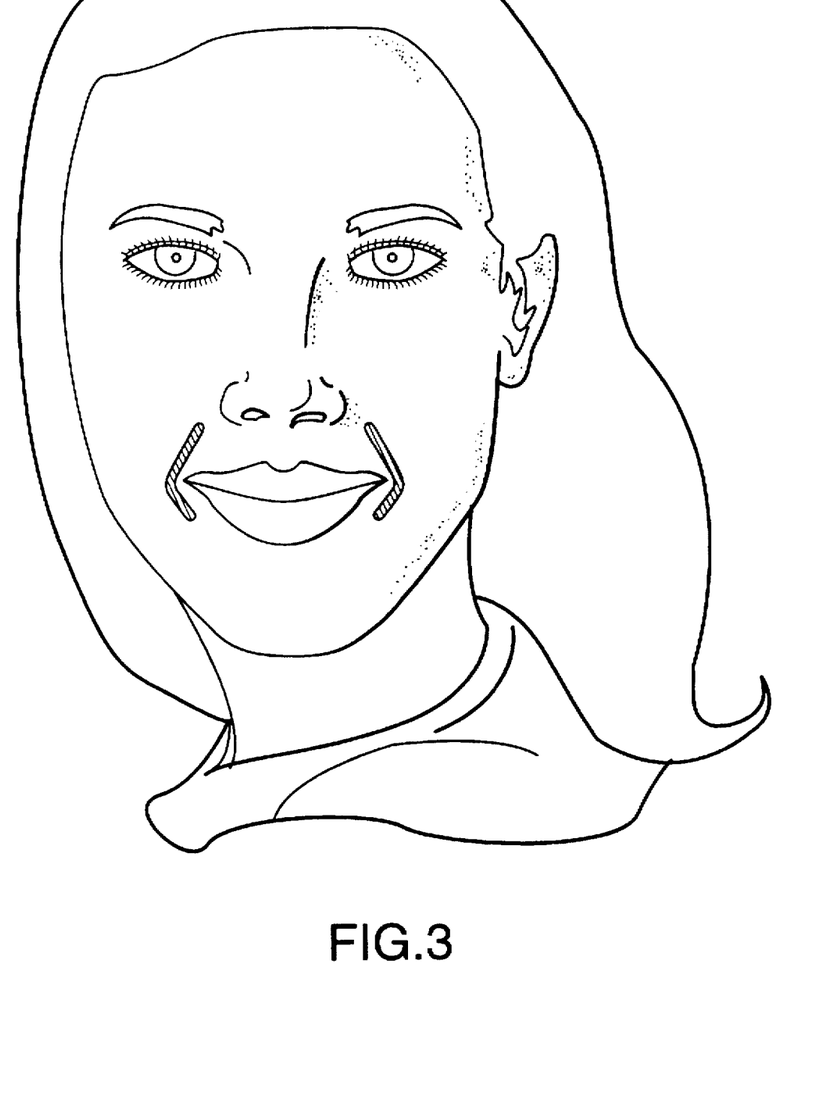
FIG. 3 illustrates a human face with a pair of the transdermal delivery devices for application of cosmetically active compositions in place in the nasolabial fold area.

For the nasolabial area, the patch is generally boomerang shaped (or an elongated kidney shape) which follows the outline of the wrinkle line falling between the nose and the corners of the mouth (see FIG. 3). The angle of the arms of the "boomerang is from about 20° to about 30° off horizontal, the width of the patch from about ½ inch to about ⅝ inch, and the length of the patch about 2 inches.

Figure 4:
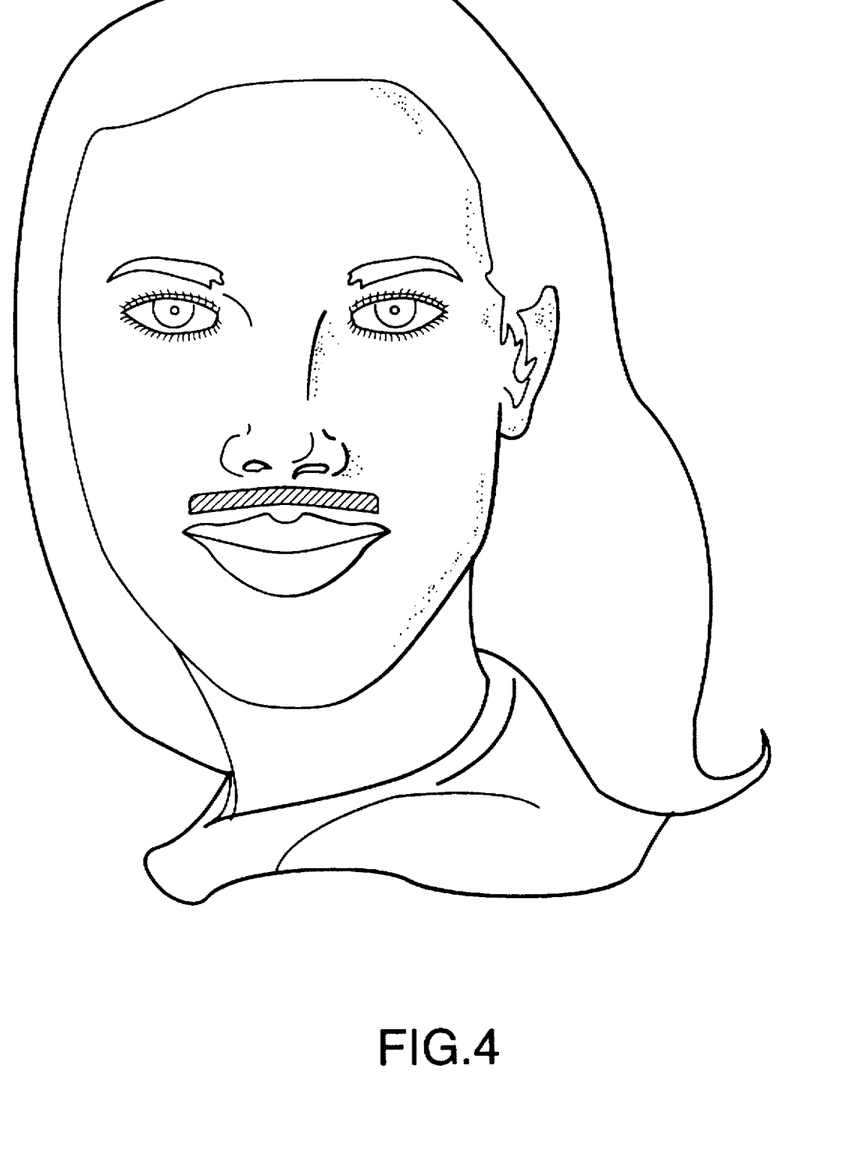
FIG. 4 illustrates a human face with the transdermal delivery device for application of cosmetically active compositions in place on the nasolabial fold area upper lip.

For improving the appearance of wrinkled skin, age spots, mottling, etc., on the upper lip, a skin care patch is applied to the upper lip (See FIG. 4). Preferably, the cosmetic patch for this application has a shape which is characterized as a narrow rectangle which is slightly curved, with dimensions of about ⅝ inch in width and about 2½ inches long, where the length is understood to be the dimension extending along the upper lip and the width is the dimension which extends from the lip toward the nose.

Figure 5A:
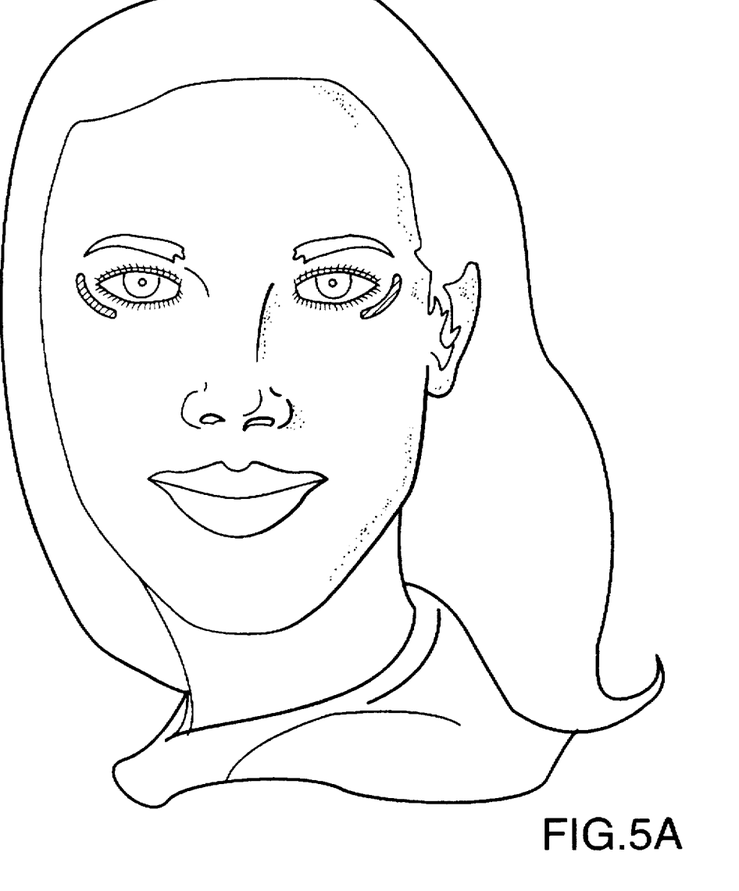
FIG. 5A illustrates a human face with a pair of the transdermal delivery devices for application of cosmetically active compositions in place at the outer corners of the eyes.
Figure 5B:
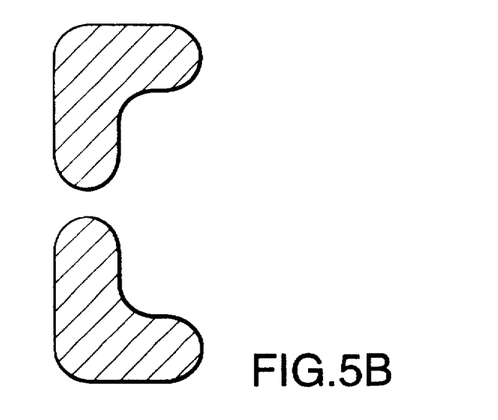
FIG. 5B illustrates the cosmetic patches for application to the outer eye corner area.
Figure 6:
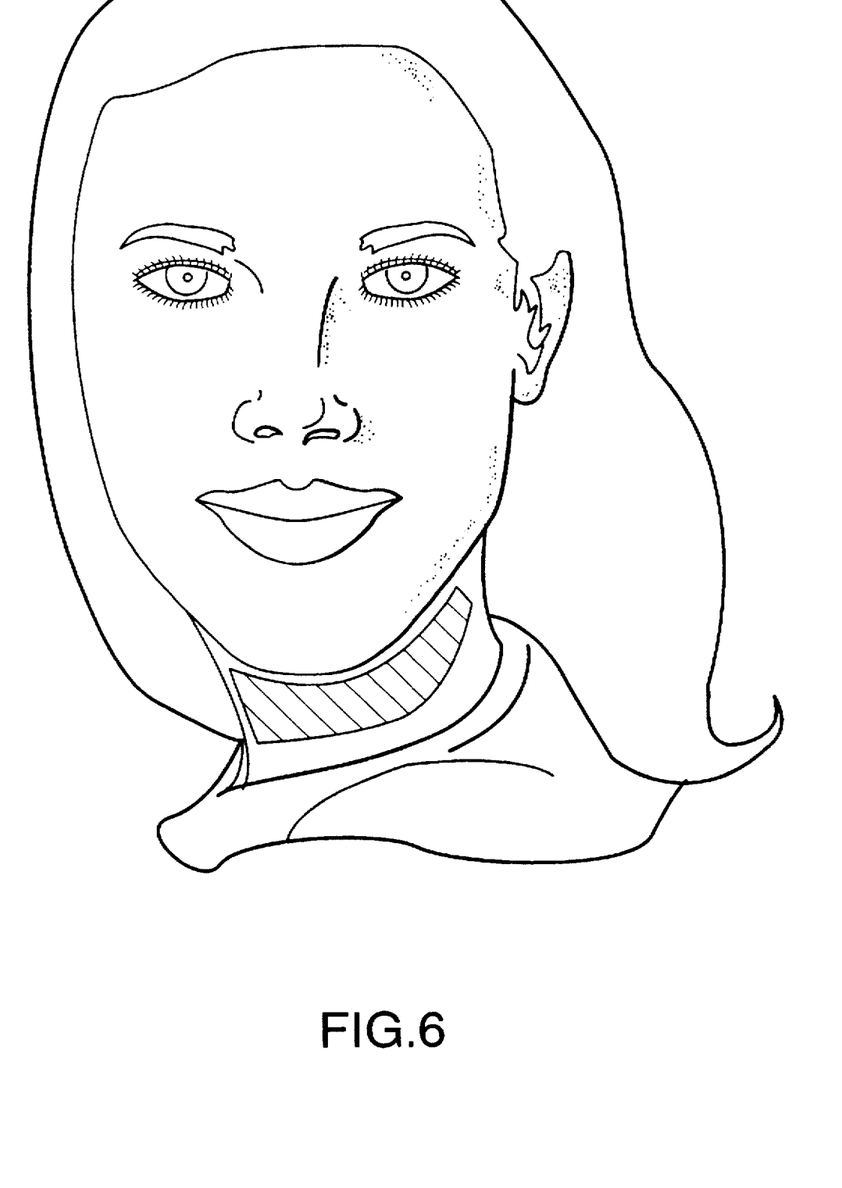
FIG. 6 illustrates a human with the transdermal delivery device for application of cosmetically active compositions in place on the neck.

For the area at the outside corners of the eyes, the cosmetic patch is preferably an elongated kidney shape, with the patch width being from about ¼ inch to about ½ inch and the length being about 1¾ inch (see FIGS. 5A–5B).

For application to the neck, the transdermal device for the percutaneous delivery of cosmetic compositions as described above is illustrated in FIG. 6. This patch is generally rectangular in shape, but slightly curved, preferably with rounded corners, and the dimensions are about 5–6 inches by 2–3 inches.

Figure 7A:
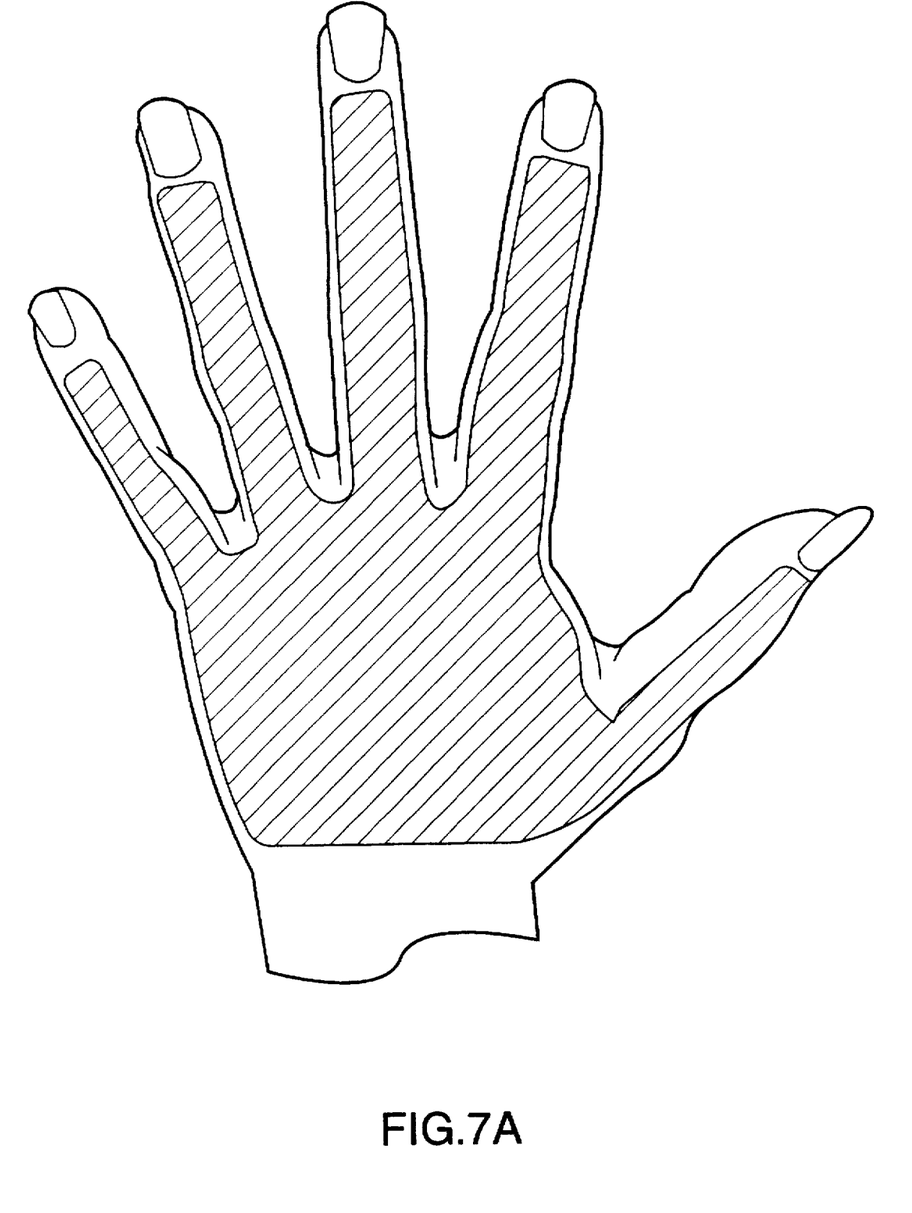
FIG. 7A–7B illustrates a human hand with the transdermal delivery device (cross-hatched) for application of cosmetically active compositions in place on the back of the hand, with extensions on the backs of the fingers and thumb in FIG. 7A and without finger extensions in FIG. 7B.
Figure 7B:
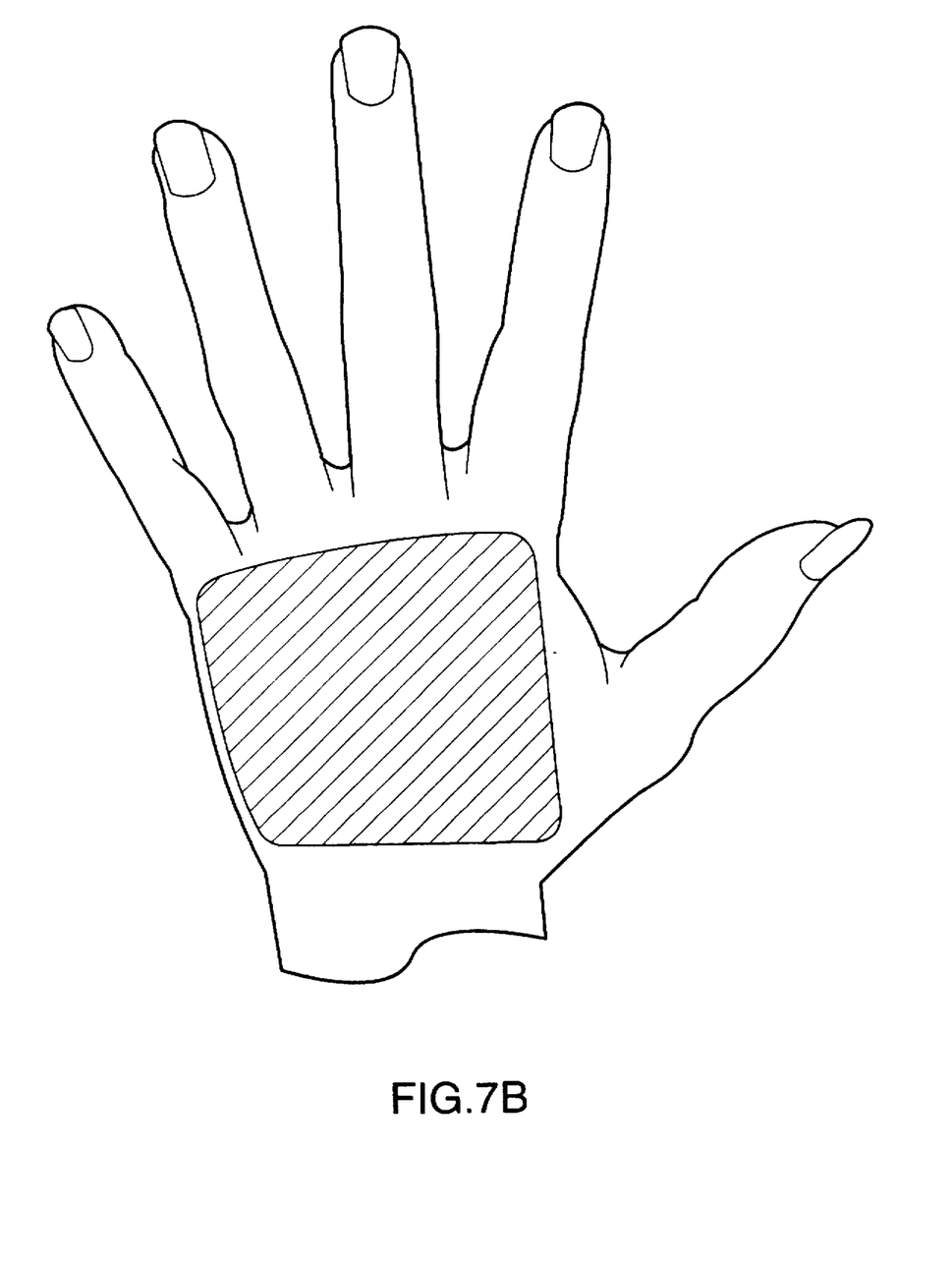

For application for the back of the hand, the cosmetic patch is shaped as illustrated in FIGS. 7A and 7B. This patch is generally square (about 2.5–3 inches), with rounded corners (FIG. 7B). Optionally there can be five extensions to cover the backs of the fingers and thumb (FIG. 7A).

The patches of desired shape can be produced from a larger sheet, with release liner, of adhesive material containing the cosmetically active ingredients in an adhesive matrix and/or any permeability enhancers and/or anti-irritants, by knife edge (cutting), gravure (printing) or other processes including extrusion or the active ingredient/permeability enhancer may be sprayed onto a backing material. Preferably, the active ingredients are mixed with the adhesive before application to the backing material.

The following examples are provided for illustrative purposes, and they are not intended to limit the scope of the invention as claimed herein. Any variations in the exemplified compositions and methods which occur to the skilled artisan are intended to fall within the scope of the present invention.

EXAMPLE 1

Silicone Pressure Sensitive Adhesive (PSA) Preparation

A silicone pressure sensitive adhesive is prepared by condensing at 115° to 120° C., in the presence of 0.025 parts anhydrous ammonia, 66 parts of a 70 wt % xylene solution of a siloxane resin copolymer consisting essentially of $(CH_3)_3SiO_{1/2}$ units and $SiO_{4/2}$ units in a molar ratio of approximately 0.75:1 and containing approximately 2.7 weight percent hydroxyl based on solids as determined by FTIR (ASTM E-168), 28 parts of a hydroxyl-terminated polydimethylsiloxane having a viscosity of about 13,500 cP (mP·s) at 25° C. and 6 parts of xylene. Following the condensation reaction, the mixture was heated to 140° C. for 1 hour to remove any excess ammonia. This silicone pressure-sensitive adhesive was found to have an adhesion of 268 g/cm at a thickness of 1–2 mils on a mylar backing.

EXAMPLE 2

Ascorbic Acid-Silicone PSA Preparations

Three formulations have been prepared containing 50/50 (weight/weight) adhesive and ascorbic acid. The formulations are described below:

EXAMPLE 2.1

A silicone pressure sensitive adhesive is prepared by condensing at 115° to 120° C., in the presence of 0.025 parts anhydrous ammonia, 67 parts of a 70 wt % xylene solution of a siloxane resin copolymer consisting essentially of $(CH^3)^3SiO_{1/2}$ units and $SiO_{4/2}$ units in a molar ratio of approximately 0.75:1 and containing approximately 2.7 weight percent hydroxyl based on solids as determined by FTIR (ASTM E-168), 31 parts of a hydroxyl terminated polydimethylsiloxane having a viscosity of about 13,500 cP (mp·s) at 25° C. and 2 parts of xylene. Following the condensation reaction, the mixture was heated to 140° C. for 1 hour to remove any excess ammonia.

The silicone adhesive mass was then mixed with an equal weight of ascorbic acid (ultra fine powder, Hoffman-LaRoche) for 17 minutes using a Lee stainless steel tilt kettle with a built-in Eppinbach high shear mixer.

To produce adhesive laminates, the adhesive solutions are coated onto fluoropolymer coated release liner, SCOTCH PAK 1022 Release Liner (SCOTCHPAK, trade mark of 3M Company, St. Paul, Minn.) using a motorized adhesive coater (model no. 33782-6, RK Print-Coat Instruments, Ltd., Litlington, Royston, Herts, U.K.) and a smooth coating bar (Dow Corning Corp., Midland, Mich.) at a speed of 165 inches/minute to yield an approximately 1.8 mil (±0.2 mil) dry adhesive thickness and allowed to air dry overnight to allow evaporation of solvents. A sheet of heat sealable polyester film laminate (SCOTCHPAK 1220, trademark of 3M Company, St. Paul, Minn.) is then transfer-coated and smoothed using a laminating roller (Laminating Rubber-covered Steel Roller, 3.25 in diameter×1.75 in weighing about 4.5 lb, U.S. Testing Co., Hoboken, N.J.) and eliminating air entrapment. This preparation is then treated with a 4.5 lb, 1.8" wide rubber-coated roller (Pressure Sensitive Tape Council, Glenview, Ill.) to insure complete contact of the three layers. The resulting laminates contain a dry adhesive layer approximately 3–5 mil in thickness. This silicone pressure-sensitive adhesive/Vitamin C composition was found to have an adhesion of 136 g/cm at 1–2 mils on a mylar backing. When this patch was applied to the skin or a surface, some adhesive remained on the skin when the patch was removed. However, it is believed that this will result in a suitable composition if a primer is used on the mylar backing.

EXAMPLE 2.2

A silicone pressure sensitive adhesive is prepared by condensing at 115° to 120° C., in the presence of 0.01 parts anhydrous ammonia, 61 parts of a 70 wt % xylene solution of a siloxane resin copolymer consisting essentially of $(CH_3)_3SiO_{1/2}$ units and $SiO_{4/2}$ units in a molar ratio of approximately 0.75:1 and containing approximately 2.7 weight percent hydroxyl based on solids as determined by FTIR (ASTM E-168), 32 parts of a hydroxyl-terminated polydimethylsiloxane having a viscosity of about 13,500 cP (mP·s) at 25° C. and 7 parts of xylene. Following the condensation reaction the mixture was heated to 140° C. for 1 hour to remove any excess ammonia. Equal weights of ascorbic acid and adhesive were mixed as above, and then laminated to films as described above.

This silicone pressure-sensitive adhesive/Vitamin C preparation was found to have an adhesion of 99 g/cm at 1–2 mils on a mylar backing. No residue was left on the skin of test 10 volunteers.

EXAMPLE 2.3

A silicone pressure adhesive is prepared by condensing at 115° to 120° C., in the presence of 0.01 parts anhydrous ammonia, 63 parts of a 70% xylene solution (w/w) of a siloxane resin copolymer consisting essentially of $(CH_3)_3SiO_{1/2}$ units and $SiO_{4/2}$ units in a molar ratio of approximately 0.75:1 and containing approximately 2.7 weight percent hydroxyl based on solids as determined by FTIR (ASTM EI-68), 37 parts of a hydroxyl-terminated polydimethylsiloxane having a viscosity of about 13,500 cP (mP·s) at 25° C. and 7 parts of xylene. Following the condensation reaction the mixture was heated to 140° C. for 1 hour to remove any excess ammonia. Equal weights of ascorbic acid and adhesive were mixed as above, and then laminated to films as described above.

This silicone pressure-sensitive adhesive/Vitamin C preparation was found to have an adhesion of 1–500 g/cm at 1–2 mils thickness on a mylar backing.

EXAMPLE 3

50 parts (as dry weight) of medical grade acrylic pressure sensitive adhesive (Draize scale score 0–1), dissolved in ethyl acetate and toluene, is mixed with 50 parts of (ascorbic acid and sodium ascorbate, both as dry powders, in a 1:22 (wt/wt) ratio) to form the cosmetically effective adhesive matrix. It is then cured at 250° F.

This adhesive matrix material is coated onto release liner (4.6 mil thickness of coating) and backing substrate laminate is applied as described hereinabove.

When tested on a human volunteer, this transdermal patch had suitable adhesive properties and suitable score on the Dermal Scoring Code (between 0 and 1). Moreover, this patch ameliorated the appearance of wrinkling near the outer corners of the eye of a man 45 years old.

What is claimed is:

1. A method of treating skin to lessen or reduce wrinkling, comprising: removing a release liner from a dermal delivery device, the delivery device including a layer having adhesive and powdered or granulated ascorbic acid with an acidity between pH 4 and pH 7, an oxygen impermeable release liner backing on a first side of the layer, and a release liner on a second side of the layer opposite the first side; applying the delivery device to the skin by contacting the layer with the skin and applying an application force to the backing to adhere the device to the skin; allowing moisture from the skin to contact the layer to infuse the ascorbic acid into the skin to lessen or reduce skin wrinkling; and removing the delivery device from the skin.

2. The treatment method of claim 1, wherein the layer further includes pH-adjusting ascorbate salts.

3. The treatment method of claim 2, wherein the ascorbate salts include sodium ascorbate.

4. The treatment method of claim 3, wherein the layer has an acidity between pH 5 and pH 6.

5. The treatment method of claim 4, wherein the layer has an acidity of approximately pH 5.5.

6. The method of claim 1, wherein the ascorbic acid has a concentration of over 60%.

7. The method of claim 1, wherein the ascorbic acid a has a concentration of over 80%.

8. The method of claim 6, wherein the ascorbic acid is buffered with powdered or granulated ascorbate salts to produce an acidity compatible with human skin.

9. A dermal delivery device for topical application of a treatment for skin wrinkles, said device comprising a backing substrate, a matrix containing powdered or granulated ascorbic acid for lessening or reducing skin wrinkles, said matrix having an acidity between pH 4 and pH 7 and an adhesive suitable for facial skin use, said matrix being atop said backing substrate, and a release liner contacted on said matrix, wherein said delivery device has a shape adapted for a target area selected from the group consisting of the upper lip, the nasolabial fold area, the lower forehead, the front portion of the neck, the outer corners of the eyes, underneath the eyes and the back of the hands.

10. The delivery device of claim 9, wherein said matrix further includes at least one of ascorbate salts, tocopherol and β-carotene.

11. The delivery device of claim 9 wherein said matrix further includes a permeability enhancing agent suitable for facial skin use selected from the group consisting of palmitic acid, and isopropyl palmitate.

12. The delivery device of claim 11 wherein said permeabilizing agent is isopropyl palpitate.

13. The delivery device of claim 9 wherein said matrix includes ascorbic acid and sodium ascorbate in a ratio by weight of from about 1:20 to about 1:25.

14. The delivery device of claim 9 wherein said matrix includes ascorbic acid and sodium ascorbate in a ratio by weight of about 1:22.

15. The delivery device of claim 9 wherein said matrix includes ascorbic acid and an ascorbate salt in proportions such that an acidity of from about pH 4 to about pH 7 is achieved.

16. The delivery device of claim 15 wherein said ascorbic acid and said ascorbate salt are present in proportions such that an acidity of from about pH 5 to about pH 6 is achieved.

17. The delivery device of claim 9 wherein the shape adapted for application to the upper lip is that of a narrow and slightly curved rectangle, about 0.625 inches in width and about 2.5 inches long and wherein the corners are rounded.

18. The delivery device of claim 9 wherein the shape adapted for application to the front of the neck is a slightly curved rectangle with rounded corners, between 5 and 6 inches in length and between 2 and 3 inches in width.

19. The delivery device of claim 9 wherein the shape adapted for application to the nasolabial fold area is an elongated kidney shape, about 2 inches in length and between 0.5 and 0.625 inches in width.

20. The delivery device of claim 9 wherein the shape adapted for application to the outer corners of the eyes is an elongated kidney shape, about 1.75 inches in length and between 0.25 and 0.5 inches in width.

21. The delivery device of claim 9 wherein the shape adapted for application to the lower forehead is a slightly curved rectangle, about 5 to 6 inches in length and between 1 and 1.75 inches in width, said rectangle having rounded corners and said rectangular further comprising a generally chevron shape at one edge of the length.

* * * * *